United States Patent
Wilcken (10) Patent No.: US 9,322,776 B2
(45) Date of Patent: Apr. 26, 2016

(54) METHOD AND SYSTEM FOR IMAGING A TARGET

(71) Applicant: The Boeing Company, Chicago, IL (US)

(72) Inventor: Stephen Kerry Wilcken, Des Moines, WA (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 14/463,004

(22) Filed: Aug. 19, 2014

(65) Prior Publication Data

US 2016/0054221 A1 Feb. 25, 2016

(51) Int. Cl.
*G01N 21/47* (2006.01)

(52) U.S. Cl.
CPC ........ *G01N 21/4738* (2013.01); *G01N 2201/02* (2013.01); *G01N 2201/061* (2013.01); *G01N 2201/0636* (2013.01); *G01N 2201/06113* (2013.01)

(58) Field of Classification Search
CPC .............. G01N 21/47; G01N 21/4738; G01N 2201/0637; G01J 1/0474
USPC ........................... 356/236, 445–448; 250/228
See application file for complete search history.

(56) References Cited

U.S. PATENT DOCUMENTS

| | | | | |
|---|---|---|---|---|
| 3,790,781 A * | 2/1974 | Horl et al. ..................... | 250/310 |
| 4,360,275 A * | 11/1982 | Louderback .................. | 356/446 |
| 4,578,584 A * | 3/1986 | Baumann et al. .......... | 250/341.4 |
| 4,988,205 A * | 1/1991 | Snail ............................. | 356/446 |
| 5,430,540 A * | 7/1995 | Ohkubo .................... | G01J 1/04 250/228 |
| 5,659,397 A * | 8/1997 | Miller et al. .................. | 356/446 |
| 5,912,741 A * | 6/1999 | Carter et al. .................. | 356/445 |
| 6,982,794 B1 * | 1/2006 | Davis et al. .................... | 356/446 |
| 7,283,222 B1 * | 10/2007 | Ohkubo ..................... | G01J 1/04 356/213 |
| 7,869,046 B2 | 1/2011 | Wilcken | |
| 2008/0252892 A1 * | 10/2008 | Pralle .................. | G01N 21/0303 356/440 |
| 2010/0296082 A1 * | 11/2010 | Ohkubo ..................... | G01J 1/02 356/236 |
| 2014/0002825 A1 * | 1/2014 | Kawate ................ | G01N 21/474 356/446 |
| 2014/0362377 A1 * | 12/2014 | Hegstrom ............ | G01N 21/474 356/343 |

OTHER PUBLICATIONS

Hubert Kostal et al., "Application of Imaging Sphere for BSDF Measurements of Arbitrary Materials", White Paper, Radiant Zemax, LLC, 2013, pp. 1-6.
Hubert Kostal et al., "Application of Imaging Sphere for BSDF Measurements of Arbitrary Materials", Illumination Modeling Workshop at the 2008 Frontiers in Optics/Laser Science XXIV Conference, Oct. 19-23, 2008, pp. 1-3.
Unknown Author, "Imaging Sphere for Scatter and Appearance Measurement IS-SA™", Radiant Zemax, LLC, 2012, pp. 1-2.

* cited by examiner

*Primary Examiner* — Hoa Pham
(74) *Attorney, Agent, or Firm* — MH2 Technology Law Group, LLP (57) ABSTRACT

A system for characterizing a bi-directional reflectance distribution function scattered light pattern of a portion of a sample is disclosed. The system can comprise a hemispherical member comprising an reflective inner surface; an entrance port operable to receive electromagnetic radiation from an electromagnetic radiation source; a first reflective optical element operable to receive at least a portion of the electromagnetic radiation and to direct the at least the portion of the electromagnetic radiation onto the portion of the sample to be characterized; a wide-angle lens operable receive the electromagnetic radiation that was specularly reflected and diffusely scattered from the portion of the sample onto the inner surface of the hemispherical member; and an imaging device operable to record intensity information imaged by the wide-angle lens to characterize the bi-directional reflectance distribution function scattered light pattern of the portion of the sample.

24 Claims, 4 Drawing Sheets

METHOD AND SYSTEM FOR IMAGING A TARGET

FIELD

The present disclosure is generally related to a bi-directional reflectance distribution function instrument, and more particularly is related to a bi-directional reflectance distribution function instrument capable of producing measurements of a target sample.

BACKGROUND

Bi-directional reflectance distribution function ("BRDF") gives the reflectance of a target as a function of illumination geometry and viewing geometry. The BRDF depends on wavelength and is determined by the structural and optical properties of the surface. Optical and structural properties may include shadow-casting, multiple scattering, mutual shadowing, transmission, reflection, absorption and emission by surface elements, facet orientation distribution and facet density.

BRDF can be determined, for instance, for clouds, land cover, and radiometric boundaries, although the present disclosure is directed at determining the BRDF of samples or subjects that can be fit within an enclosure. Examples of these samples or subjects may include, for example, films or materials extracted from objects for study. The samples may generally have a small footprint. A number of devices exist for determining the BRDF of samples of this size.

One type of known device for determining the BRDF is a device that is known in the industry as a 2D BRDF. As the name implies, the BRDF is measured in two dimensions. However, to completely appreciate the BRDF results, a 3D image must be provided. A composite 3D image can be created, but it requires integrating many 2D images and recording the many 2D images is time intensive.

There also are 3D BRDF devices available in the marketplace. One such 3D BRDF device includes directing a collimated light beam against a sample within a white hemispherical screen and capturing an image of the scattered light pattern produced on the hemispherical screen by the sample. A problem with this system is that the white screen tends to re-scatter light onto other parts of the screen, which diminishes the reliability and accuracy of the 3D BRDF result. This secondary scattering of light from one part of the screen to other parts of the screen is known as cross talk. This approach also suffers from very low optical efficiency. Most of the light that is scattered off of the white screen will not be received by the sensor. This will either result in excessively long signal integration times of samples which exhibit very low BRDF, or will prevent measurement of low BRDF samples.

Other known 3D BRDF devices do not include an imaging screen. These other known 3D BRDF devices are significantly more expensive while producing results that are not materially more reliable than the aforementioned 3D BRDF with a white hemispherical screen.

Thus, a heretofore unaddressed need exists in the industry to address the aforementioned deficiencies and inadequacies.

SUMMARY

According to the present teachings, a system for characterizing a bi-directional reflectance distribution function scattered light pattern of a portion of a sample is disclosed. The system can comprise a hemispherical-elliptical member comprising an inner surface, the inner surface comprising an either a highly specular reflective surface or a diffusely reflective material formed thereon and operable to diffusely scatter electromagnetic radiation about a desired amount relative to a specular reflection angle; an entrance port operable to receive electromagnetic radiation from an electromagnetic radiation source; a first reflective optical element operable to receive at least a portion of the electromagnetic radiation and to direct the at least the portion of the electromagnetic radiation onto the portion of the sample to be characterized; a wide-angle lens operable to receive the electromagnetic radiation that was scattered from the portion of the sample onto the inner surface of the hemispherical member; and an imaging device operable to record intensity information imaged by the wide-angle lens to characterize the bi-directional reflectance distribution function scattered light pattern of the portion of the sample, wherein the sample is positioned at a first focus point and the imaging device is positioned at a second focus point relative to the hemispherical-elliptical member.

The system can further comprise an electromagnetic radiation source operable to produce the electromagnetic radiation, wherein the electromagnetic radiation is coherent or incoherent. For example, if the electromagnetic radiation source is the incoherent source, the system further comprises an optical filter positional between the electromagnetic source and the first reflective optical element and operable to transmit a desired range of wavelengths to be used to characterize the portion of sample.

The system can further comprise a sample support mount that is fixed or movable with one or more actuating elements.

The system can further comprise a movable second reflective optical element operable to receive electromagnetic radiation from the first reflective optical element and direct electromagnetic radiation onto the portion of the sample from one or more directions or angles.

When the system comprises the diffuse material, the desired amount can be less than 5°, less than 1°, or less than 0.5°.

When the system comprises the highly specular inner surface (mirror-like), the system can further comprise an optical mount that is arranged to support the wide-angle lens and move the wide-angle lens in one or more degrees of freedom and/or along its axis to accommodate for pupil aberration.

According the present teachings, a method of visualizing and recording a bi-directional reflectance distribution function scattered light pattern is disclosed. The method can comprise directing an electromagnetic radiation beam through an entrance port of a hemispherical-elliptical enclosure and by a first reflective optical element onto a sample; scattering the electromagnetic radiation beam from the sample onto an inner surface of the hemispherical enclosure, wherein the inner surface comprising either a highly specular (mirror-like) surface or diffusely reflective material formed thereon and operable to diffusely scatter electromagnetic radiation about a desired amount relative to a specular reflection angle; and recording the distribution of the scattered electromagnetic radiation received by a wide-angle lens by an imaging device, wherein the sample is positioned at a first focus point and the imaging device is positioned at a second focus point relative to the hemispherical-elliptical enclosure.

The recording can be performed at more than one wavelength of electromagnetic radiation. The recording can also be performed at more than one angle of incidence of the electromagnetic radiation.

According to the present teachings, a system for characterizing a bi-directional reflectance distribution function scattered light pattern of a portion of a sample is disclosed. The system can comprise a hemispherical member comprising an inner surface, the inner surface comprising a diffuse material formed thereon and operable to diffusely scatter electromagnetic radiation about a desired amount relative to a specular reflection angle; an entrance port operable to receive electromagnetic radiation from an electromagnetic radiation source; a first reflective optical element operable to receive at least a portion of the electromagnetic radiation and to direct the at least the portion of the electromagnetic radiation onto the portion of the sample to be characterized; a wide-angle lens operable to receive the electromagnetic radiation that was diffusely scattered from the portion of the sample onto the inner surface of the hemispherical member; and an imaging device operable to record intensity information imaged by the wide-angle lens to characterize the bi-directional reflectance distribution function scattered light pattern of the portion of the sample.

The system can further comprise an electromagnetic radiation source operable to produce the electromagnetic radiation, wherein the electromagnetic radiation is coherent or incoherent. If the electromagnetic radiation source is the incoherent source, the system can further comprise an optical filter positional between the electromagnetic source and the first reflective optical element and operable to transmit a desired range of wavelengths to be used to characterize the portion of sample.

The system can further comprise a sample support mount that is fixed or movable with one or more actuating elements.

The system can further comprise a movable second reflective optical element operable to receive electromagnetic radiation from the first reflective optical element and direct electromagnetic radiation onto the portion of the sample from one or more directions or angles.

The desired amount relative to a specular reflection angle is about 0.5° or about 1.0° or less than 5°.

According to the preset teachings, a method of visualizing and recording a bi-directional reflectance distribution function scattered light pattern is disclosed. The method can comprise directing an electromagnetic radiation beam through an entrance port of a hemispherical enclosure and by a first reflective optical element onto a sample; scattering the electromagnetic radiation beam from the sample onto an inner surface of the hemispherical enclosure, wherein the inner surface comprising a diffuse material formed thereon and operable to diffusely scatter electromagnetic radiation about a desired amount relative to a specular reflection angle; and recording the distribution of the scattered electromagnetic radiation received by the wide-angle lens by an imaging device.

The recording can be performed at more than one wavelength of electromagnetic radiation and/or at more than one angle of incidence of the electromagnetic radiation.

Additional objects and advantages of the disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate the present disclosure and together with the description, serve to explain the principles of the present disclosure.

DESCRIPTION

Reference will now be made in detail to exemplary implementations of the present disclosure, examples of which are illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary implementations in which the present disclosure may be practiced. These implementations are described in sufficient detail to enable those skilled in the art to practice the present disclosure and it is to be understood that other implementations may be utilized and that changes may be made without departing from the scope of the present disclosure. The following description is, therefore, merely exemplary.

Figure 1A:
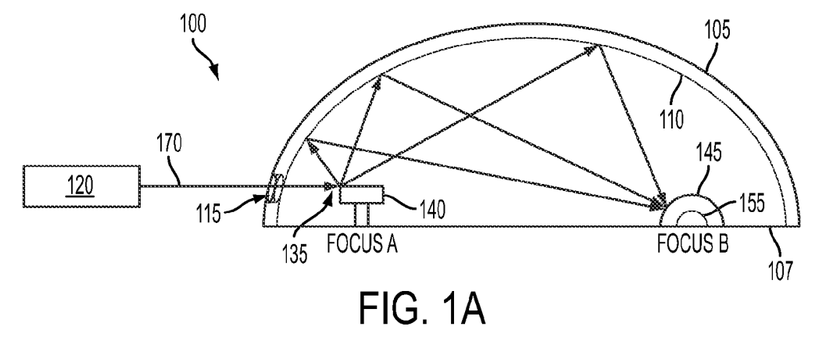
FIGS. 1A, 1B, and 1C are an example side view, top view, and side perspective view, respectively, illustration of bi-directional reflectance distribution function structure 100, in accordance the present disclosure.
Figure 1B:
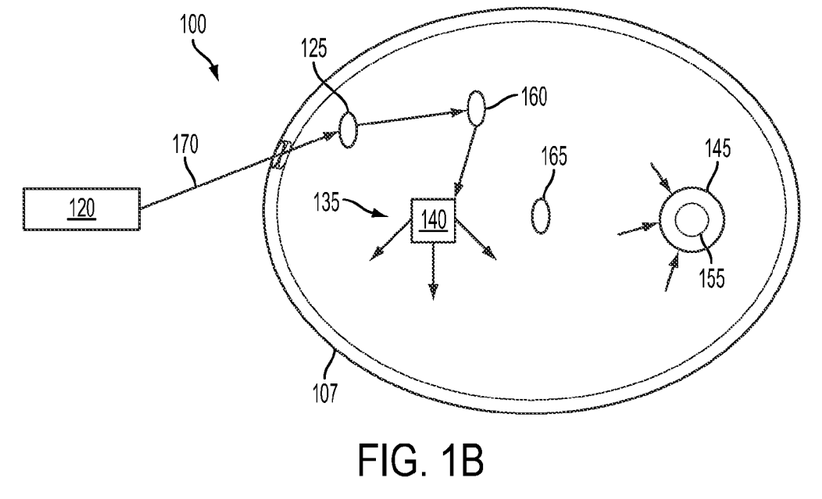
Figure 1C:
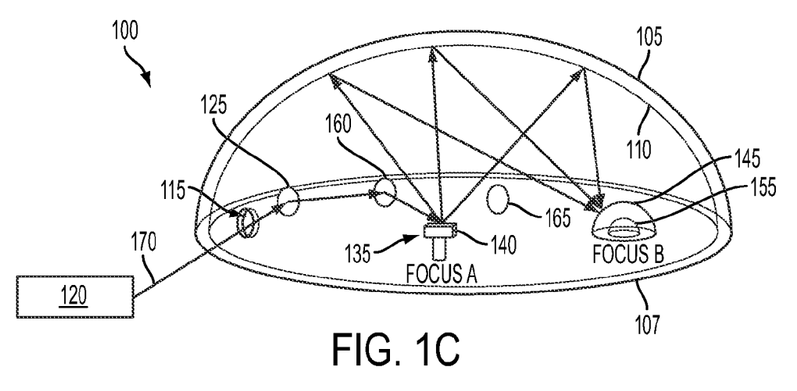

FIGS. 1A, 1B, and 1C are an example side view, top view, and side perspective view, respectively, illustration of bi-directional reflectance distribution function structure 100, in accordance the present disclosure. Structure 100 comprises a hemispherical-elliptical member or enclosure 105 comprising inner surface 110 surrounding and enclosing base member 107. Inner surface 110 can comprise a highly specular (mirror-like) surface or a diffuse reflective material that is operable to diffusely scatter electromagnetic radiation about a desired amount relative to a specular reflection angle. For example, the desired amount can be less than 5°. Base member 107 comprises a very low BRDF optical property in order to reduce or eliminate optical cross talk.

Structure 100 comprises entrance view port 115 operable to receive electromagnetic radiation 170 from electromagnetic radiation source 120. Entrance port 115 can be in the hemispherical-elliptical member 105 or base member 107. Electromagnetic radiation source (or source) 120 can be an incoherent source producing many different wavelengths of radiation or can be a coherent source, such as a conventional laser, producing a more narrow band of wavelengths. If an incoherent source is used, one or more optical filters (not shown) can be used to limit or condition the amount, quality, wavelength range that is allowed to enter structure 100. The coherent source can be a tunable laser capable of producing one or more narrow wavelength bands of radiation.

Base member 107 comprises first reflective optical element 125 that is operable to receive at least a portion of the electromagnetic radiation beam 170 and to direct at least the portion of the electromagnetic radiation beam 170 onto the portion 135 of sample 140 to be characterized. Base member 107 also comprises a wide-angle lens 145, e.g., "fish-eye" lens, or similar type of optical component, operable to receive the electromagnetic radiation 150 that was specularly reflected and diffusely scattered from the portion of the sample onto inner surface 110 of hemispherical-elliptical member 105. Base member 107 also comprises imaging device 155, e.g., a camera, that is operable to record intensity information imaged by wide-angle lens 145 to characterize the bi-directional reflectance distribution function scattered light pattern of the portion 135 of sample 140. Imaging device 155 can include wide-angle lens 145 or they can be separate components that are suitably coupled together. Wide-angle lens 145 permits capturing a wide field-of-view image within structure 100 without a front of imaging device 155 protruding materially into structure 100. An optical mount (not shown) can support wide-angle lens 145 and be arranged to move wide-angle lens 145 in one or more degrees of freedom, including along its axis to accommodate for pupil aberrations. In this configuration, sample 140 can be positioned at a first focal position and imaging device 155 is positioned at a second focal position relative to hemispherical-elliptical member 105, such that any radiation scattered by sample 140 at one focus is reflected off inner surface 110 and brought to a focus on imaging device 155 at the second focus.

First reflective optical element 125 can be supported by an optical mount (not shown) that is in a fixed position relative to sample 140 or imaging device 155. Optionally, base member 107 can include second reflective optical element 160. Second reflective optical element 160 can be supported by another optical mount (not shown) that can be movable, using one or more actuators (not shown), in one or more degrees of freedom. Second reflective optical element 160 can be operable to receive radiation from first reflective optical element 125 and direct radiation onto a portion of sample 140 to be characterized at a variety of incident angles.

Base member 107 can also comprise one or more beam blockers, such as beam blocker 165, which can be operable to block any portion of the reflected or scattered radiation that is unwanted and not intended to be captured by imaging device 155. The one or more beam blockers can be supported by individual fixed or movable supports (not shown) that can be positioned before or during the measurement operation.

In operation, beam of electromagnetic radiation 170 is directed through entrance view port 115 toward sample 140, via first reflective optical element 125 and, optionally, second reflective optical element 160 into structure 100. At least a portion of the beam of electromagnetic radiation 170 is scattered by sample 140 toward inner surface 110 of hemispherical-elliptical member 105. Inner surface 110 reflects the scattered radiation received from sample 140. Wide-angle lens 145 receives the radiation from inner surface 110 and focuses the radiation onto imaging device 155 where the bi-directional reflectance distribution is obtained and recorded.

Figure 2:
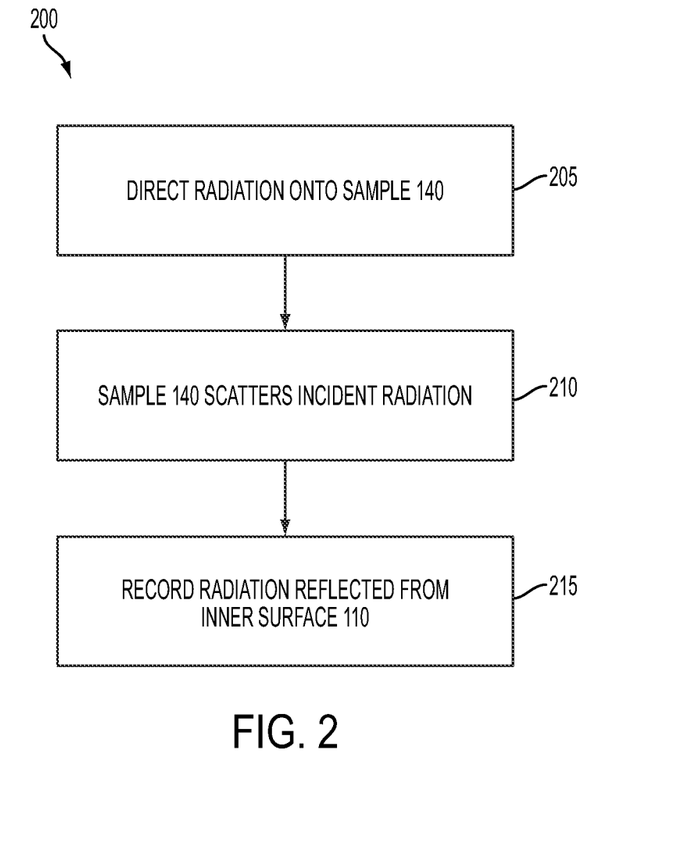
FIG. 2 is a flowchart 200 illustrating a method of utilizing the above mentioned bi-directional reflectance distribution function structure 100 in accordance with the present teachings of the disclosure.

FIG. 2 is a flowchart 200 illustrating a method of utilizing the above mentioned bi-directional reflectance distribution function structure 100 in accordance with the present teachings of the disclosure. It should be noted that any process descriptions or blocks in flow charts should be understood as representing modules, segments, portions of code, or steps that include one or more instructions for implementing specific logical functions in the process, and alternate implementations may be included in which functions may be executed out of order from that shown or discussed, including substantially concurrently or in reverse order, depending on the functionality involved, as would be understood by those reasonably skilled in the art.

As is shown at 205, beam 170 of electromagnetic radiation is directed through entrance port 115 of structure 100 and onto sample 140 located at a first focus position on base member 107. Electromagnetic radiation beam 170 scatters from sample 140 onto inner surface 110 of hemispherical-elliptical member 105, wherein inner surface 110 has formed thereon a relatively high reflectivity substantially specular (mirror-like) surface or a diffuse material that is operable to diffusely scatter electromagnetic radiation about a desired amount relative to a specular reflection angle. For example the desired amount can be less than 5°. The electromagnetic radiation is scattered by sample 140 at 210. At 215, the image of the distribution of the scattered electromagnetic radiation derived from beam 170 is received by wide-angle lens 145 and recorded by imaging device 155 located at a second focus position on base member 107. Imaging device 155 is positioned with respect to wide-angle lens 145 such that parallel light rays leaving sample 140 at a particular scattering angle, and subsequently reflecting from inner surface 110 of hemispherical-elliptical member 105, are brought to a point focus at a specific position on the focal plane of imaging device 155. Pupil aberration in the wide-angle lens 145 is accommodated by translating wide-angle lens 145 and imaging device 155 in three or four small incremental steps along the direction of the lens axis, interspersed with three or four recordings of the received electromagnetic radiation. The recorded images are then stitched together in software to yield a full hemispherical image of the scattered light pattern produced by sample 140.

Figure 3A:
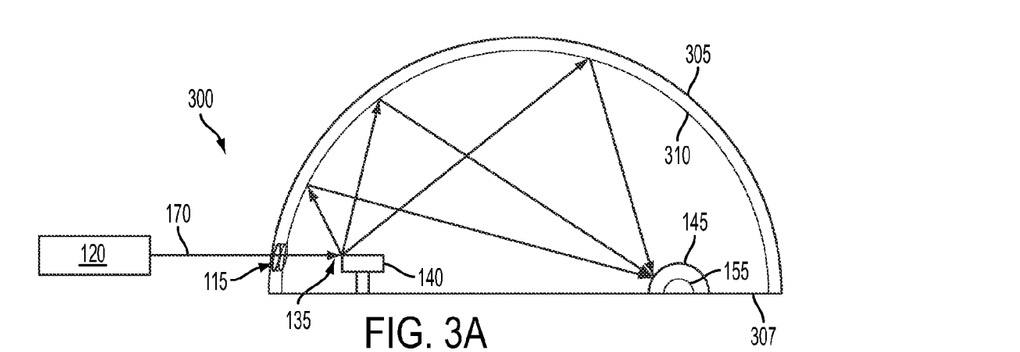
FIGS. 3A, 3B, and 3C are an example side view, top view, and side perspective view, respectively, illustration of another bi-directional reflectance distribution function structure 300, in accordance the present disclosure.
Figure 3B:
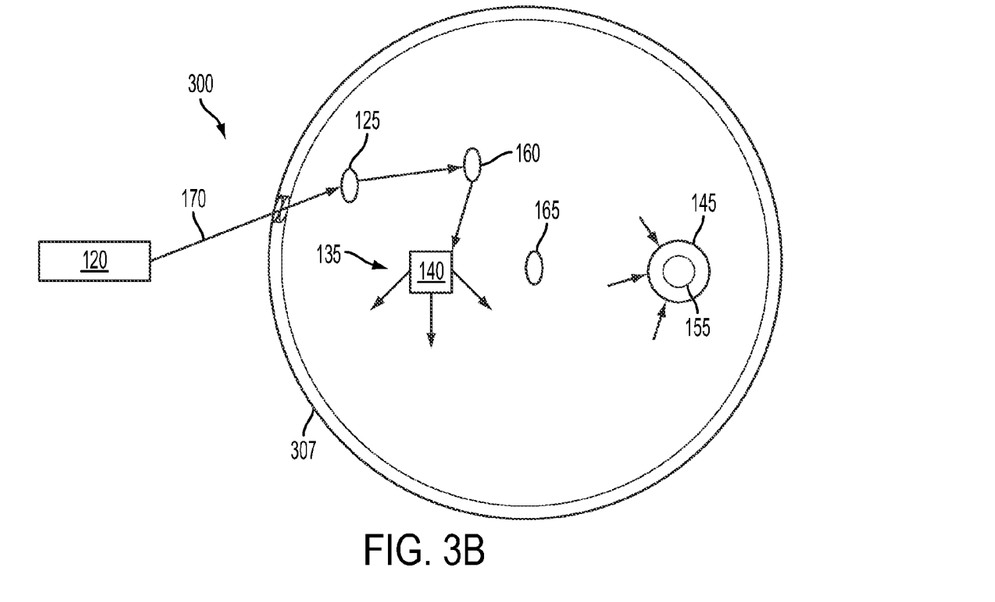
Figure 3C:
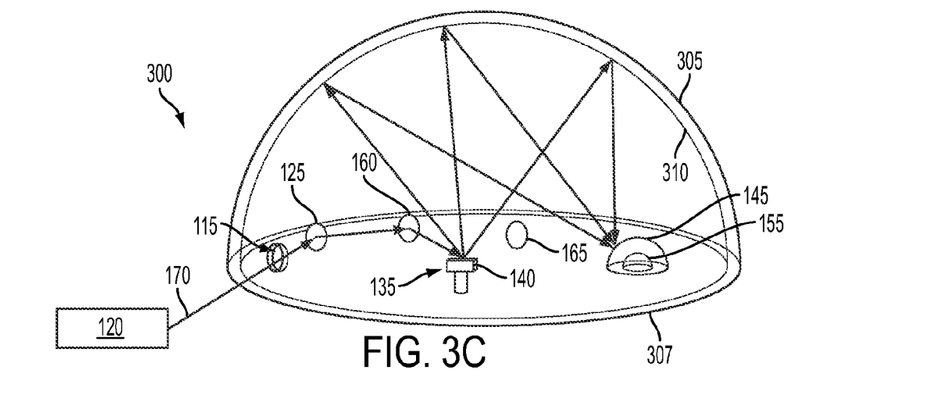

FIGS. 3A, 3B, and 3C are an example side view, top view, and side perspective view, respectively, illustration of another bi-directional reflectance distribution function structure 300, in accordance the present disclosure. Structure 300 comprises a hemispherical member or enclosure 305 comprising inner surface 310 surrounding and enclosing base member 307. Inner surface 310 comprises a diffuse material formed thereon and operable to diffusely scatter electromagnetic radiation about a desired amount relative to a specular reflection angle. For example, inner surface can reflect radiation about 0.5°, about 1.0°, about 2° around the specular reflection angle. The material of inner surface 310 can be selected to reflect other suitable amounts of radiation onto imaging device 155, discussed further below, to adequately image the hemispherical distribution of scattered light produced by sample 140. Inner surface 310 can have a relatively high reflectivity substantially non-specular surface, with light scattering characteristics similar to a movie screen, but very highly peaked about the specular direction, i.e., in the direction of wide-angle lens 145 and imaging device 155. This highly optimized coating on inner surface 310 of enclosure 305 will, thus, greatly improve optical efficiency, and enable measurement of samples with extremely low BRDF at reasonable signal integration times. Further, the optimized BRDF characteristics of the coating on inner surface 310 will offset the impact of spherical aberration associated with hemispherical enclosure 305. Wide-angle lens 145 will be adjusted with respect to imaging device 155 such that points on inner surface 310 of hemispherical enclosure 305 will be in focus on the image plane of imaging device 155. Base member 107 comprises a very low BRDF optical property in order to reduce or eliminate optical cross talk.

Hemispherical member 305 or base member 307 comprises entrance port 115 operable to receive electromagnetic radiation 170 from electromagnetic radiation source 120. Electromagnetic radiation source (or source) 120 can be an incoherent source producing many different wavelengths of radiation or can be a coherent source, such as a conventional laser, producing a more narrow band of wavelengths. If an incoherent source is used, one or more optical filters (not shown) can be used to limit or condition the amount, quality, wavelength range that is allowed to enter structure 100. The coherent source can be a tunable laser capable of producing one or more narrow wavelength bands of radiation.

Base member 307 comprises first reflective optical element 125 that is operable to receive at least a portion of the electromagnetic radiation 130 and to direct the at least the portion of the electromagnetic radiation 130 onto the portion 135 of sample 140 to be characterized. Base member 307 also comprises a wide-angle lens 145 operable to receive the electromagnetic radiation 150 that was specularly reflected and diffusely scattered from portion 135 of sample 140 onto inner surface 310 of hemispherical member 305. Base member 307 also comprises imaging device 155 that is operable to record intensity information imaged by wide-angle lens 145, e.g., "fish-eye" lens, or similar type of optical component, to characterize the bi-directional reflectance distribution function scattered light pattern of portion 135 of sample 140. Imaging device 155 can include wide-angle lens 145 or they can be separate components that are suitably coupled together. Wide-angle lens 145 permits capturing a wide field-of-view image within structure 100 without a front of the camera protruding materially into structure 300.

Again, as in the arrangement shown in FIGS. 1A, 1B, and 1C, first reflective optical element 125 can be supported by optical mount (not shown) that is in a fixed position relative to the sample 140 or imaging device 155. Optionally, structure 300 can include second reflective optical element 160. Second reflective optical element 160 can be supported by another optical mount (not shown) that can be movable, using one or more actuators (not shown), in one or more degrees of freedom. Second reflective optical element 160 can be operable to receive radiation from first reflective optical element 125 and direct radiation onto portion 135 of sample 140 to be characterized.

Base member 307 can also comprise one or more beam blockers, such as beam blocker 165, which can be operable to block any portion of the reflected or scattered radiation that is unwanted and not intended to be captured by imaging device 155. The one or more beam blockers can be supported by individual fixed or movable supports (not shown) that can be positioned before or during the measurement operation.

In operation, beam of electromagnetic radiation 170 is directed through entrance view port 115 toward sample 140, via first reflective optical element 125 and, optionally, second reflective optical element 160 into structure 300. At least a portion of the beam of electromagnetic radiation 170 is scattered by sample 140 toward inner surface 310 of hemispherical member 305. Inner surface 310 reflects the scattered radiation received from sample 140. Wide-angle lens 145 receives the radiation from inner surface 310 and focuses the radiation onto imaging device 155 where the bi-directional reflectance distribution is obtained and recorded.

Figure 4:
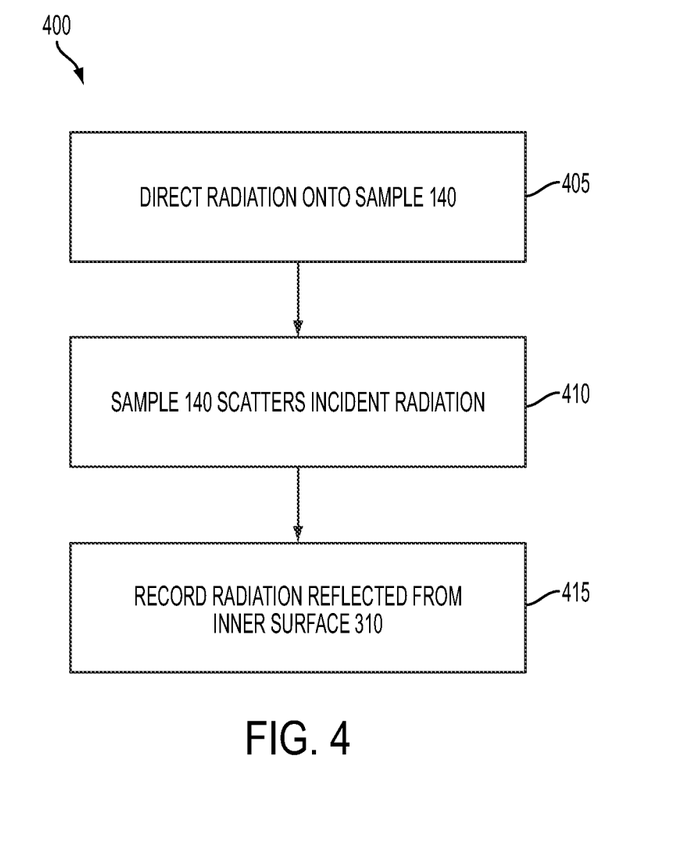
FIG. 4 is a flowchart 400 illustrating a method of utilizing the above mentioned bi-directional reflectance distribution function structure 300 in accordance with the present teachings of the disclosure

FIG. 4 is a flowchart 400 illustrating a method of utilizing the above-mentioned bi-directional reflectance distribution function structure 300 in accordance with the present teachings of the disclosure. It should be noted that any process descriptions or blocks in flow charts should be understood as representing modules, segments, portions of code, or steps that include one or more instructions for implementing specific logical functions in the process, and alternate implementations may be included in which functions may be executed out of order from that shown or discussed, including substantially concurrently or in reverse order, depending on the functionality involved, as would be understood by those reasonably skilled in the art.

As is shown at 405, beam 170 of electromagnetic radiation is directed through entrance view port 115 of structure 300 and onto sample 140 on base member 307. Electromagnetic radiation beam 170 scatters from sample 140 onto inner surface 310 of hemispherical member 305, wherein inner surface 310 has formed thereon a relatively high reflectivity substantially non-specular surface. The electromagnetic radiation is scattered by sample 140 at 410. At 415, the image of the distribution of the scattered electromagnetic radiation derived from beam 170 is received by wide-angle lens 145 and recorded by imaging device 155 on base member 307.

For example, inner surface 110 and/or 310 can comprise a reflective holographic light shaping diffuser material made by Luminit, LLC of Torrance, Calif. Other suitable materials for inner surface 110 and/or 310 can be used as is known in the art.

Multiple images can be acquired of sample 140 at different incident angles and/or different wavelengths using structure 100 or 300. For example, source 120 can be capable of producing different ranges of radiation wavelengths or different electromagnetic radiation sources can be used to produce beam 170. Once multiple images of the distribution of the electromagnetic radiation have been captured, the images may be stitched together utilizing conventional image processing software. Furthermore, samples which have known or well understood optical scattering characteristics (e.g., samples coated with a reflectance calibration standard such as Spectrolon®, available from Labsphere, Inc., North Sutton, N.H.) may be used as reference standards. The process of recording the BRDF of the standard, and the use of such recorded BRDF data for removing or accommodating instrumental characteristics of the enclosure and data recording mechanisms through standard data renormalization or rectification procedures, will be familiar to those skilled in the art.

For simplicity and illustrative purposes, the principles of the present teachings are described by referring mainly to example implementations thereof. However, one of ordinary skill in the art would readily recognize that the same principles are equally applicable to, and can be implemented in, all types of information and systems, and that any such variations do not depart from the true spirit and scope of the present teachings. Moreover, in the foregoing detailed description, references are made to the accompanying figures, which illustrate specific example implementations. Electrical, mechanical, logical and structural changes may be made to the example implementations without departing from the spirit and scope of the present teachings. The foregoing detailed description is, therefore, not to be taken in a limiting sense and the scope of the present teachings is defined by the appended claims and their equivalents.

The terms and descriptions used herein are set forth by way of illustration only and are not meant as limitations. For example, although methods has been described in top to bottom fashion, the steps of the method may be performed in a different order than illustrated or simultaneously. Furthermore, to the extent that the terms "including", "includes", "having", "has", "with", or variants thereof are used in either the detailed description or the claims, such terms are intended to be inclusive in a manner similar to the term "comprising." As used herein, the term "one or more of" with respect to a listing of items such as, for example, A and B, means A alone, B alone, or A and B. Those skilled in the art will recognize that these and other variations are possible.

Other implementations consistent with the present teachings will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A system for characterizing a bi-directional reflectance distribution function scattered light pattern of a portion of a three-dimensional sample, the system comprising:
   a hemispherical-elliptical member comprising an inner surface, the inner surface comprising a non-specular reflective material formed thereon;
   an entrance port operable to receive electromagnetic radiation from an electromagnetic radiation source;
   a first reflective optical element operable to receive at least a portion of the electromagnetic radiation and to direct the at least the portion of the electromagnetic radiation onto the portion of the three-dimensional sample to be characterized;
   a wide-angle lens operable to receive the electromagnetic radiation that was scattered from the portion of the three-dimensional sample onto the inner surface of the hemi-spherical-elliptical member; and
   an imaging device that protrudes into the hemispherical-elliptical member and is operable to record intensity information imaged by the wide-angle lens to characterize the bi-directional reflectance distribution function scattered light pattern of the portion of the three-dimensional sample based, at least in part, on a standard sample having a predetermined optical scattering characteristic,
   wherein the three-dimensional sample protrudes into the hemispherical-elliptical member and is positioned at a first focus point and the imaging device is positioned at a second focus point relative to the hemispherical-elliptical member.

2. The system according to claim 1, further comprising the electromagnetic radiation source operable to produce the electromagnetic radiation, wherein the electromagnetic radiation is coherent or incoherent.

3. The system according to claim 2, wherein the electromagnetic radiation source is the incoherent source, the system further comprising an optical filter positional between the electromagnetic source and the first reflective optical element and operable to transmit a desired range of wavelengths to be used to characterize the portion of three-dimensional sample.

4. The system according to claim 1, further comprising a sample support mount that is fixed or movable with one or more actuating elements.

5. The system according to claim 1, further comprising a movable second reflective optical element operable to receive electromagnetic radiation from the first reflective optical element and direct electromagnetic radiation onto the portion of the three-dimensional sample from one or more directions or angles.

6. The system according to claim 1, further comprising an optical mount arranged to support the wide-angle lens and move the wide-angle lens along one or more degrees of freedom to accommodate for pupil aberration.

7. A system for characterizing a bi-directional reflectance distribution function scattered light pattern of a portion of a three-dimensional sample, the system comprising:
   a hemispherical-elliptical member comprising an inner surface, the inner surface comprising a diffusely reflective material formed thereon and operable to diffusely scatter electromagnetic radiation about a desired amount relative to a specular reflection angle;
   an entrance port operable to receive electromagnetic radiation from an electromagnetic radiation source;
   a first reflective optical element operable to receive at least a portion of the electromagnetic radiation and to direct the at least the portion of the electromagnetic radiation onto the portion of the three-dimensional sample to be characterized;
   a wide-angle lens operable to receive the electromagnetic radiation that was scattered from the portion of the three-dimensional sample onto the inner surface of the hemi-spherical member; and
   an imaging device that protrudes into the hemispherical-elliptical member and is operable to record intensity information imaged by the wide-angle lens to characterize the bi-directional reflectance distribution function scattered light pattern of the portion of the three-dimensional sample based, at least in part, on a standard sample having a predetermined optical scattering characteristic,
   wherein the three-dimensional sample protrudes into the hemispherical-elliptical member and is positioned at a first focus point and the imaging device is positioned at a second focus point relative to the hemispherical-elliptical member.

8. The system according to claim 7, wherein the desired amount is less than 5°.

9. A method of visualizing and recording a bi-directional reflectance distribution function scattered light pattern of a three-dimensional sample, the method comprising:
   directing an electromagnetic radiation beam through an entrance port of a hemispherical-elliptical enclosure and by a first reflective optical element onto the three-dimensional sample;
   scattering the electromagnetic radiation beam from the three-dimensional sample onto an inner surface of the hemispherical enclosure, wherein the inner surface comprising a non-specular reflective material formed thereon;
   recording the distribution of the scattered electromagnetic radiation received by a wide-angle lens by an imaging device that protrudes into the hemispherical-elliptical enclosure at more than one incident angle and at more than one wavelength of the electromagnetic radiation;
   determining the bi-directional reflectance distribution function of the three-dimensional sample based on the recording of more than one image of the sample based, at least in part, on a standard sample having a predetermined optical scattering characteristic, and
   wherein the three-dimensional sample protrudes into the hemispherical-elliptical enclosure and is positioned at a first focus point and the imaging device is positioned at a second focus point relative to the hemispherical-elliptical enclosure.

10. The method according to claim 9, wherein the recording is performed at more than one wavelength of electromagnetic radiation.

11. The method according to claim 9, wherein the recording is performed at more than one angles of incidence of the electromagnetic radiation.

12. The method according to claim 9, further comprising moving the wide-angle lens along one or more degrees of freedom to accommodate for pupil aberration.

13. A method of visualizing and recording a bi-directional reflectance distribution function scattered light pattern of a three-dimensional sample, the method comprising:
   directing an electromagnetic radiation beam through an entrance port of a hemispherical-elliptical enclosure and by a first reflective optical element onto the three-dimensional sample;

scattering the electromagnetic radiation beam from the three-dimensional sample onto an inner surface of the hemispherical enclosure, wherein the inner surface comprising a diffusely reflective material formed thereon and operable to diffusely scatter electromagnetic radiation about a desired amount relative to a specular reflection angle;

recording the distribution of the scattered electromagnetic radiation received by a wide-angle lens by an imaging device that protrudes into the hemispherical-elliptical enclosure at more than one incident angle and at more than one wavelength of the electromagnetic radiation;

determining the bi-directional reflectance distribution function of the three-dimensional sample based on the recording of more than one image of the sample based, at least in part, on a standard sample having a predetermined optical scattering characteristic, and wherein the three-dimensional sample protrudes into the hemispherical-elliptical enclosure and is positioned at a first focus point and the imaging device is positioned at a second focus point relative to the hemispherical-elliptical enclosure.

14. The method according to claim 13, wherein the desired amount is less than 5°.

15. A system for characterizing a bi-directional reflectance distribution function scattered light pattern of a portion of a three-dimensional sample, the system comprising:

a hemispherical member comprising an inner surface, the inner surface comprising a diffuse material formed thereon and operable to diffusely scatter electromagnetic radiation about a desired amount relative to a specular reflection angle;

an entrance port operable to receive electromagnetic radiation from an electromagnetic radiation source;

a first reflective optical element operable to receive at least a portion of the electromagnetic radiation and to direct the at least the portion of the electromagnetic radiation onto the portion of the three-dimensional sample to be characterized;

a wide-angle lens operable to receive the electromagnetic radiation that was diffusely scattered from the portion of the three-dimensional sample onto the inner surface of the hemispherical member; and an imaging device that protrudes into the hemispherical member and is operable to record intensity information imaged by the wide-angle lens to characterize the bi-directional reflectance distribution function scattered light pattern of the portion of the three-dimensional sample based, at least in part, on a standard sample having a predetermined optical scattering characteristic, wherein the sample protrudes into the hemispherical member.

16. The system according to claim 15, further comprising the electromagnetic radiation source operable to produce the electromagnetic radiation, wherein the electromagnetic radiation is coherent or incoherent.

17. The system according to claim 16, wherein the electromagnetic radiation source is the incoherent source, the system further comprising an optical filter positional between the electromagnetic source and the first reflective optical element and operable to transmit a desired range of wavelengths to be used to characterize the portion of three-dimensional sample.

18. The system according to claim 15, further comprising a sample support mount that is fixed or movable with one or more actuating elements.

19. The system according to claim 15, further comprising a movable second reflective optical element operable to receive electromagnetic radiation from the first reflective optical element and direct electromagnetic radiation onto the portion of the three-dimensional sample from one or more directions or angles.

20. The system according to claim 15, wherein the desired amount relative to the specular reflection angle is less than 5°.

21. A method of visualizing and recording a bi-directional reflectance distribution function scattered light pattern of a three-dimensional sample, the method comprising:

directing an electromagnetic radiation beam through an entrance port of a hemispherical enclosure and by a first reflective optical element onto the three-dimensional sample;

scattering the electromagnetic radiation beam from the three-dimensional sample onto an inner surface of the hemispherical enclosure, wherein the inner surface comprising a diffuse material formed thereon and operable to diffusely scatter electromagnetic radiation about a desired amount relative to a specular reflection angle;

recording the distribution of the scattered electromagnetic radiation received by a wide-angle lens by an imaging device at more than one incident angle and at more than one wavelength of the electromagnetic radiation; and determining the bi-directional reflectance distribution function of the three-dimensional sample based on the recording of more than one image of the sample based, at least in part, on a standard sample having a predetermined optical scattering characteristic.

22. The method according to claim 21, wherein the recording is performed at more than one wavelength of electromagnetic radiation.

23. The method according to claim 21, wherein the recording is performed at more than one angles of incidence of the electromagnetic radiation.

24. The method according to claim 21, wherein the desired amount relative to the specular reflection angle is less than 5°.

* * * * *